(12) United States Patent
Roux et al.

(10) Patent No.: US 12,213,482 B2
(45) Date of Patent: Feb. 4, 2025

(54) FUNGICIDE ENHANCERS EFFECTIVE FOR TREATING PLANTS INFECTED WITH FUNGAL PATHOGENS

(71) Applicants: Board of Regents, The University of Texas System, Austin, TX (US); Cottongen, LLC, Austin, TX (US)

(72) Inventors: Stanley J. Roux, Austin, TX (US); Gregory B. Clark, Austin, TX (US); Simon L. Hiebert, Austin, TX (US)

(73) Assignees: Board of Regents, The University of Texas System, Austin, TX (US); Cottongen, LLC, Austin, TX (US)

(*) Notice: Subject to any disclaimer, the term of this patent is extended or adjusted under 35 U.S.C. 154(b) by 498 days.

(21) Appl. No.: 17/407,959

(22) Filed: Aug. 20, 2021

(65) Prior Publication Data

US 2022/0039381 A1  Feb. 10, 2022

Related U.S. Application Data

(62) Division of application No. 15/547,008, filed as application No. PCT/US2016/015077 on Jan. 27, 2016, now Pat. No. 11,129,383.

(60) Provisional application No. 62/108,114, filed on Jan. 27, 2015.

(51) Int. Cl.
| | |
|---|---|
| A01N 41/02 | (2006.01) |
| A01N 37/02 | (2006.01) |
| A01N 37/26 | (2006.01) |
| A01N 41/06 | (2006.01) |
| A01N 43/16 | (2006.01) |
| A01N 43/653 | (2006.01) |
| A01N 59/20 | (2006.01) |
| C12N 5/04 | (2006.01) |

(52) U.S. Cl.
CPC .............. *A01N 41/02* (2013.01); *A01N 37/02* (2013.01); *A01N 37/26* (2013.01); *A01N 41/06* (2013.01); *A01N 43/16* (2013.01); *A01N 43/653* (2013.01); *A01N 59/20* (2013.01); *C12N 5/04* (2013.01); *A01N 2300/00* (2013.01)

(58) Field of Classification Search
CPC ........ A01N 37/00; A01N 41/00; A01N 43/00; A01N 2300/00
See application file for complete search history.

(56) References Cited

U.S. PATENT DOCUMENTS

| | | | |
|---|---|---|---|
| 6,448,472 | B1 | 9/2002 | Thomas et al. |
| 11,129,383 | B2 * | 9/2021 | Roux ..................... A01N 41/02 |
| 2002/0077365 | A1 | 6/2002 | Windsor et al. |
| 2002/0103082 | A1 | 8/2002 | Windsor et al. |
| 2002/0173031 | A1 | 11/2002 | Thomas et al. |
| 2003/0008369 | A1 | 1/2003 | Windsor et al. |
| 2006/0027633 | A1 | 2/2006 | Miyake |
| 2006/0276339 | A1 | 12/2006 | Windsor et al. |
| 2010/0305161 | A1 | 12/2010 | Bosselaers et al. |

FOREIGN PATENT DOCUMENTS

| | | |
|---|---|---|
| JP | 2002529378 A | 9/2002 |
| JP | 2003531154 A | 10/2003 |
| JP | 2007522187 A | 8/2007 |
| WO | 0166792 A1 | 9/2001 |
| WO | 0220726 A2 | 3/2002 |
| WO | 2005014777 A2 | 2/2005 |
| WO | 2012167023 | 12/2012 |
| WO | 2013071824 B1 | 5/2013 |

OTHER PUBLICATIONS

International Search Report and Written Opinion for PCT/US2016/015077 dated Apr. 21, 2016.
Windsor et al., "Automated colorimetric screen for apyrase inhibitors," Biotechniques, 33(5):1028-1030, 2002.
Windsor et al., "Multiherbicide tolerance conferred by AtPgp1 and apyrase overexpression in *Arabidopsis thaliana*," Nat Biotechnol, 21(4):428-433, 2003.
Extended European Search Report regarding European Application No. 16744015, dated Jun. 4, 2018.
Coleman et al., "Efflux in Fungi: La Piece de Resistance," PLOS Pathogens 5(6):1-7, 2009.

OTHER PUBLICATIONS

Reimann et al., "Inhibition of Efflux Transporter-Mediated Fungicide Resistance in Pyrenophora tritici-repentis by a Derivative of 4'-Hydroxyflavone and Enhancement of Fungicide Activity," Applied and Environmental Microbiology 71(6):3269-3275, 2005.
Tripathy et al., "Apyrase inhibitors enhance the ability of diverse fungicides to inhibit the growth of different plant-pathogenic fungi," Molecular Plant Pathology 18(7):1012-1023, 2017.
Kumar et al. "Apyrase inhibitors enhance the ability of diverse fungicides to inhibit the growth of different plant-pathogenic fungi," Mol. Plant Pathol. Sep. 2017;18(7):1012-23, PMID: 27392542. (Year: 2017).
Indonesian Office Action regarding Indonesian App. No. P00201705655, May 28, 2024.

* cited by examiner

*Primary Examiner* — Theodore R. Howell
(74) *Attorney, Agent, or Firm* — Dentons US LLP

(57) ABSTRACT

The present invention includes compositions and methods of for treating plants infected with fungal pathogens by contacting an infected plant or plant at risk of infection with a fungicidal composition comprising an fungicide selected from copper compound such as copper octanoate or copper hydroxide, or a triazole fungicide such as myclobutanil, propionazole, tebuconazole or epoxiconazole, an enhancer selected from apyrase inhibitors, e.g., N-(m-tolyl)-[1,1'-biphenyl]-4-sulfonamide, S-heptyl 2-oxo-2H-chromene 3-carbothioate, 3-(N-(4-bromophenyl) sulfamoyl)-N-(3-nitrophenyl)benzamide, or (E)-3-methyl-N-(1-(naphthalen-2-yl) ethylidene)benzohydrazide and, optionally, a phytologically-acceptable inert carrier.

11 Claims, 7 Drawing Sheets

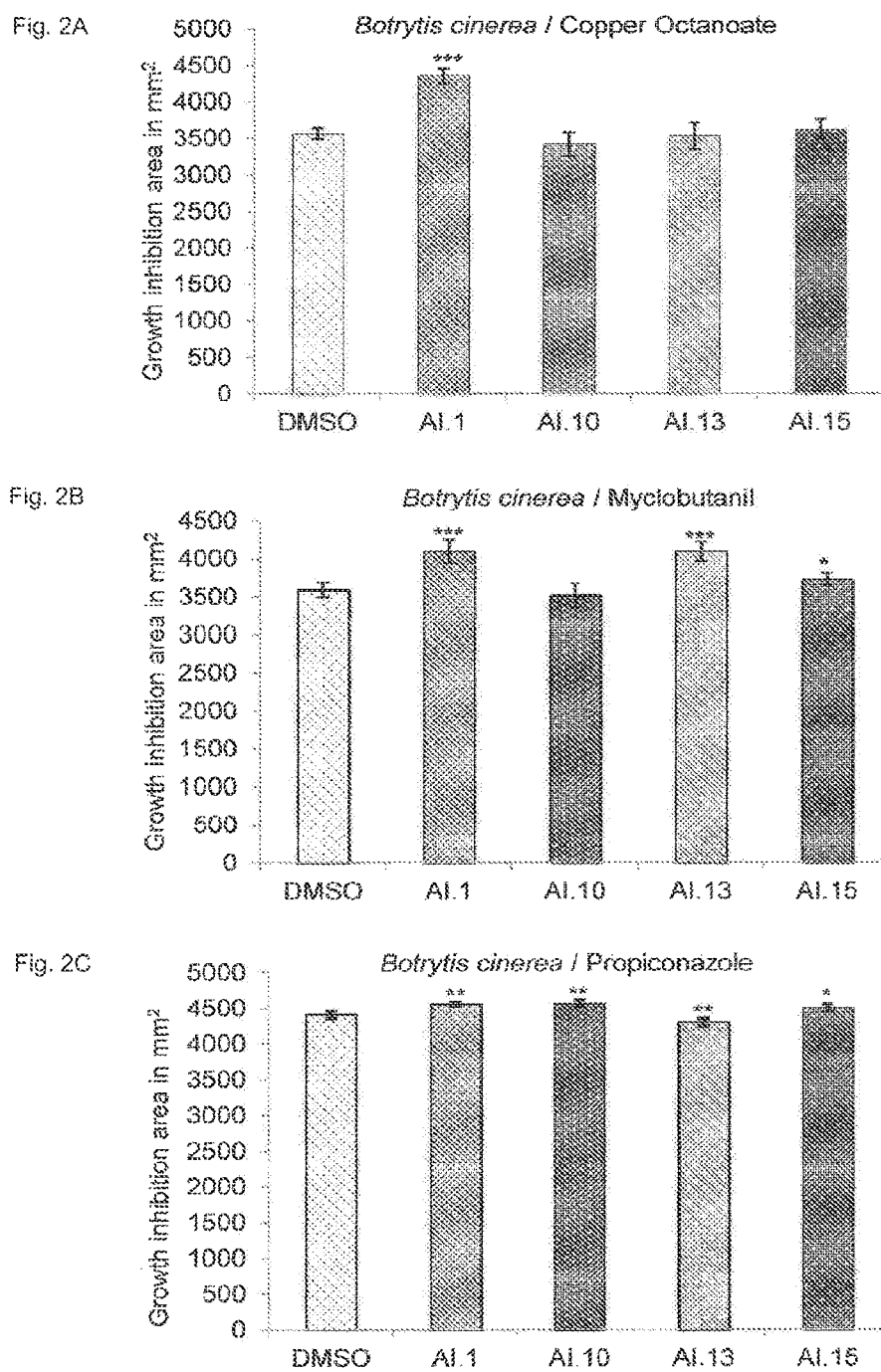

Fig. 7
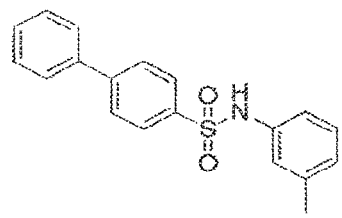
Formula: $C_{19}H_{17}NO_2S$
NAME: N-(m-tolyl)-[1,1'-biphenyl]-4-sulfonamide
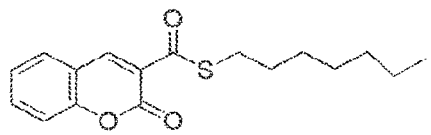
Formula: $C_{17}H_{20}O_3S$
NAME: S-heptyl 2-oxo-2H-chromene-3-carbothioate
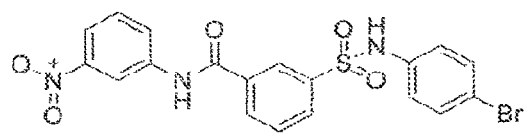
Formula: $C_{19}H_{14}N_3O_5SBr$
NAME: 3-(N-(4-bromophenyl)sulfamoyl)-N-(3-nitrophenyl)benzamide
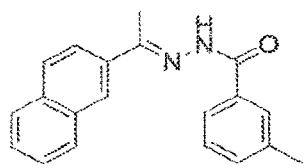
Formula: $C_{20}H_{18}N_2O$
NAME: (E)-3-methyl-N'-(1-(naphthalen-2-yl)ethylidene)benzohydrazide

FUNGICIDE ENHANCERS EFFECTIVE FOR TREATING PLANTS INFECTED WITH FUNGAL PATHOGENS

CROSS-REFERENCE TO RELATED APPLICATIONS

This application is a divisional of U.S. application Ser. No. 15/547,008, filed Jul. 27, 2017, which issued as U.S. Pat. No. 11,129,383 on Sep. 28, 2021, which application is a 371 National Stage application of International Application No. PCT/US2016/015077, filed Jan. 27, 2016 (expired), which claims the benefit of, and priority to, U.S. Provisional Patent Application Ser. No. 62/108,114, filed Jan. 27, 2015, the entire contents of which are hereby incorporated by reference in their entireties.

TECHNICAL FIELD OF THE INVENTION

The present invention relates in general to the field of fungicides, and more particularly, to the enhanced efficacy of fungicides for the treatment of plants infected with fungal pathogens.

BACKGROUND ART

Without limiting the scope of the invention, this background is described in connection with fungicide compositions useful to treat plants infected with fungal pathogens.

Fungal pathogens cause devastating losses of crops and postharvest fruits worldwide (Chen et al., 2008). Many chemical fungicides have been used in high doses and frequent intervals to prevent these losses by killing different fungal species. The global market for fungicides was estimated to be over 7.4 billion in 2005 (Morton and Staub, 2008) and expected to rise to over $20 billion by 2017 (Israel, 2013). To reduce the risk of crop disease and enhance the safety of food and protect the environment, new effective fungicides or strategies to increase the potency of current fungicides should be developed.

One limitation to the potency of fungicides is the ability of fungi to quickly detoxify them by sequestering them or exporting them across the plasma membrane. Fungi use diverse mechanisms for removing xenobiotics, and it is clear that any inhibition of these processes would increase the potency of fungicides. Plants also detoxify xenobiotics by exporting them. A prior report documented that overexpression of either an ABCB1 homologue (AtPgp1) or an apyrase (NTPDase) enzyme (AtAPY1) conferred multiherbicide resistance to *A. thaliana* plants (Windsor et al., 2003). Furthermore, inhibitors of apyrase enzyme activity suppressed plants' ability to export herbicides and thus increased their sensitivity to these toxins (Windsor et al., 2003). A key function of certain apyrases is to help maintain a low steady state of extracellular ATP (eATP) (Knowles, 2011; Lim et al., 2014), which is a known regulator of diverse responses in plants and animals (Clark et al., 2014). Taken together, the data of Windsor et al. (2003) supported a dual role for apyrases and ABC transporters in herbicide resistance, and indicated that disruption of apyrase activity or exogenous addition of ATP could inhibit ABC transport activity and thus block the continued efflux of toxic compounds.

SUMMARY OF THE INVENTION

The apyrase inhibitors AI.1 {N-(m-tolyl)-[1,1'-biphenyl]-4-sulfonamide}, AI.10 {S-heptyl 2-oxo-2H-chromene-3-carbothioate}, AI.13 {-(N-(4-bromophenyl) sulfamoyl)-N-(3-nitrophenyl) benzamide}, and AI.15 {(E)-3-methyl-N'-(1-(naphthalen-2-yl)ethylidene) benzohydrazide} differentially enhance the effect of copper and triazole fungicides against plant pathogenic fungi. Preferred fungicides that are susceptible to enhancement are copper octanoate, copper hydroxide, myclobutanil, propiconazole, tebuconazole, epoxiconazole, difenoconazole, triconazole, and prothioconazole. The combination of the select fungicide and enhancer provides synergistic fungicidal activity against plant pathogenic fungi.

In one embodiment, the present invention includes compositions and methods of treating plants or plant seeds infected with or at risk of being infected with a fungal pathogen. The compositions of this present invention comprise a formulation of a fungicide and an enhancer and a phytologically-acceptable inert carrier. The fungicides are selected from a copper compound fungicide or triazole fungicide, such as copper octanoate, copper hydroxide, myclobutanil, propiconazole, tebuconazole, epoxiconazole, difenoconazole, triconazole, or prothioconazole. Examples of the apyrase inhibitor used as enhancers include:
  AI.1: N-(m-tolyl)-[1,1'-biphenyl]-4-sulfonamide,
  AI.10: S-heptyl 2-oxo-2H-chromene-3-carbothioate,
  AI.13: 3-(N-(4-bromophenyl) sulfamoyl)-N-(3-nitrophenyl)benzamide, or
  AI.15: (E)-3-methyl-N'-(1-(naphthalen-2-yl)ethylidene) benzohydrazide.

In the composition of this invention, the weight ratio or the fungicide to enhancer at which the fungicidal effect is synergistic lies within the range of between about 500:1 and 5000:1.

Another embodiment of the invention is directed to treatment of plants or plant seeds infected with or at risk with infection by plant pathogenic fungi. The treatment involves contacting the plant with a formulation of the fungicide and enhancer, wherein the fungicide is copper octanoate, copper hydroxide, myclobutanil, propiconazole, tebuconazole, epoxiconazole, difenoconazole, triconazole, or prothioconazole and the enhancer is AI.1, AI.10, AI.13 or AI.15. The formulations of the present invention are particular effective against the plant fungal pathogens *Botrytis cinerea, Colletotrichum graminicola, Fusarium oxysporum, Sclerotiana sclerotiorum, Verticillium dahlia, Mycospharella gramincola* and *Sphacelatheca reliana*.

In another embodiment, the present invention includes a fungicide comprising: a copper or triazole fungicide; and an apyrase inhibitor in amounts sufficient to treat a fungus. In one aspect, the apyrase inhibitor is selected from at least one of N-(m-tolyl)-[1,1'-biphenyl]-4-sulfonamide; S-heptyl 2-oxo-2H-chromene-3-carbothioate; 3-(N-(4-bromophenyl) sulfamoyl)-N-(3-nitrophenyl) benzamide; 3-(N-(4-bromophenyl) sulfamoyl)-N-(3-nitrophenyl)benzamide; or (E)-3-methyl-N'(1-(naphthalen-2-yl) ethylidene)benzohydrazide. In another aspect, the fungicide is added to a growth media for growing cells. In another aspect, the cells are selected from at least one of bacterial, fungal, plant, animal, mammalian, yeast, amphibian, avian, nematode or insect cells. In another aspect, the composition is synergistic and the weight ratio of the fungicide to the apyrase inhibitor is between about 500:1 and 5000:1.

Yet another embodiment, the present invention includes a method of treating infection by a fungal pathogen that is resistant to a copper class or triazole fungicide, the method comprising: contacting the fungal pathogen with a composition comprising a copper class or triazole in combination with a fungal apyrase inhibitor, wherein the fungal apyrase inhibitor prevents the fungus from at least one of detoxifying the fungicide or exporting the fungicide. In one aspect, the fungicide is selected from at least one of copper octanoate, propiconazole, tebuconazole, or epoxiconazole. In another aspect, the fungal pathogen is a plant pathogen selected from at least one of *Botrytis cinerea, Colletotrichum graminicola, Fusarium oxysporum, Sclerotiana sclerotiorum, Verticillium dahlia, Mycospharella gramincola,* or *Sphacelotheca reliana*. In another aspect, the fungal pathogen is a plant pathogen and a plant treated is a fruit bearing plant, vegetable hearing plant, nut bearing plant or grain plant. In another aspect, the fungal pathogen is a plant pathogen and a plant treated is strawberry, banana, corn, soybean, tobacco, wheat or cotton. In another aspect, the composition is synergistic and the weight ratio of the fungicide to the apyrase inhibitor is between about 500:1 and 5000:1.

DESCRIPTION OF THE DRAWINGS

For a more complete understanding of the features and advantages of the present invention, reference is now made to the detailed description of the invention along with the accompanying figures and in which:

FIGS. 2A to 2C are graphs that show that Apyrase Inhibitors differentially enhance the potency of three different fungicides. 2A. Copper Octanoate, 2B. Propiconazole, and 2C. Myclobutanil against the pathogenic fungi *Botrytis cinerea*. Plant pathogenic fungi strain (*Botrytis cinerea*) were grown in YPD medium petri dish in the presence of 65 µM of apyrase inhibitors (AI #1, 10, 13 and 15) at 30° C. for 12 days. The equivalent volume of dimethylsulphoxide (DMSO) was added as a control. The studies were repeated two times with similar results. Error bars indicate standard deviations (n=5). The significances of the potency of fungicides are indicated: * (Student's t-test, P<0.001);  (Student's t-test, P<0.01) or *(Student's t-test, P<0.05).

FIG. 7 shows exemplary chemical structures and systematic names of the studied apyrase inhibitors (AI).

DETAILED DESCRIPTION OF THE INVENTION

Figure 1:
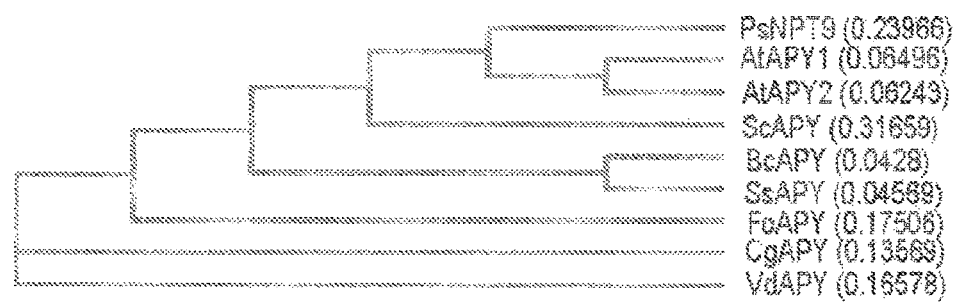
FIG. 1 is adendrogram showing the phylogenetic relationship between apyrase characterized from different plants and Fungi species. The tree was constructed based on the amino acid sequences deduced from apyrase gene sequences reported from different plants and fungi: *Arabidopsis thaliana* apyrase 1 (Accession No. NP_187058), *Arabidopsis thaliana* apyrase 2 (Accession No. NP_001154717), *Pisum sativum* (Accession No. BAA75506), *Botrytis cinerea* (Accession No. XP_001558134), *Colletotrichum graminicola* (Accession No. EFQ33146), *Fusarium oxysporum* (Accession No. ENH75262), *Sclerotiana scleratiorum* (Accession No. XP_001590729) and *Verticillium dahliae* (Accession No. EGY20804).
Figure 3A:
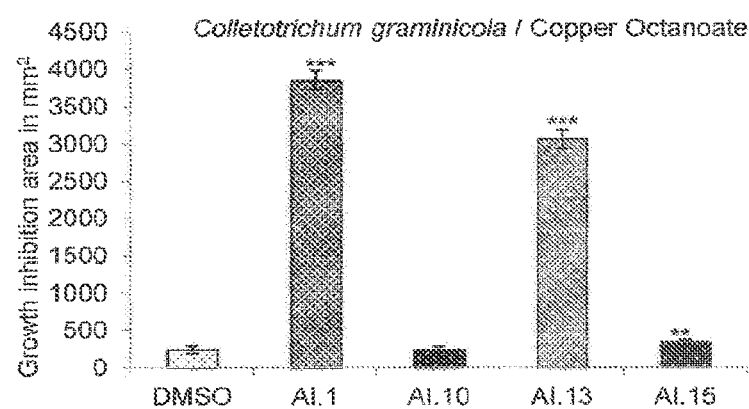
FIGS. 3A to 3C are graphs that show that Apyrase Inhibitors differentially enhance the potency of three different fungicides 3A. Copper Octanoate, 3B. Propiconazole, and 3C. Myclobutanil against the pathogenic fungi *Colletotrichum graminicola*. Plant pathogenic fungi strain (*Colletotrichum* were grown in YPD medium petri dish in the presence of 65 µM of apyrase inhibitors (AI #1, 10, 13 and 15) at 30° C. for 7 days. The equivalent volume of dimethylsulphoxide (DMSO) was added as a control. The studies were repeated two times with similar results. Error bars indicate standard deviations (n=5). The significances of the potency of fungicides are indicated: * (Student's t-test, P<0.001; (Student's t-test, P<0.01) or *(Student's t-test, P<0.05).
Figure 3B:
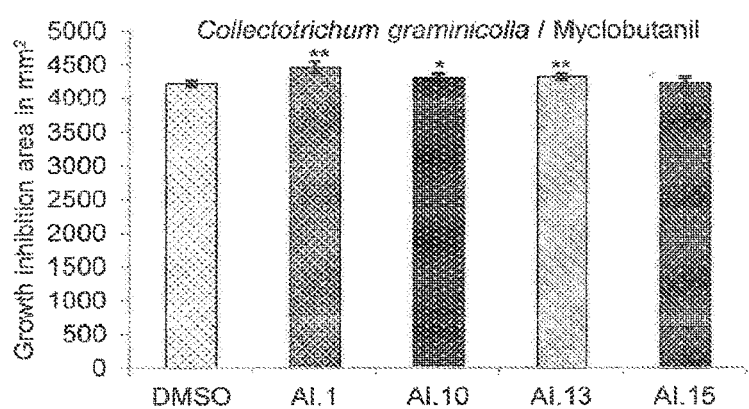
Figure 3C:
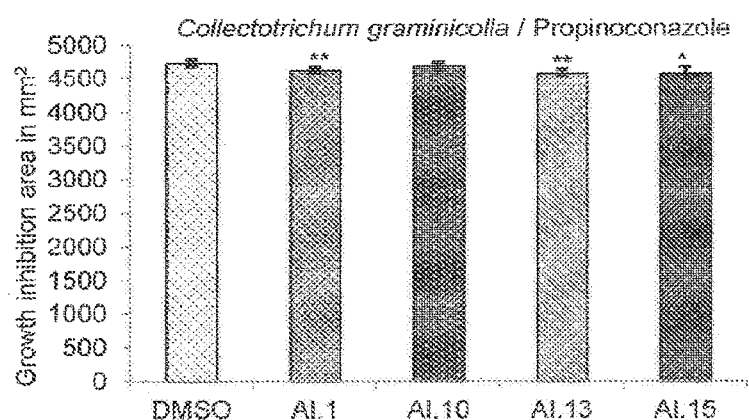
Figure 4A:
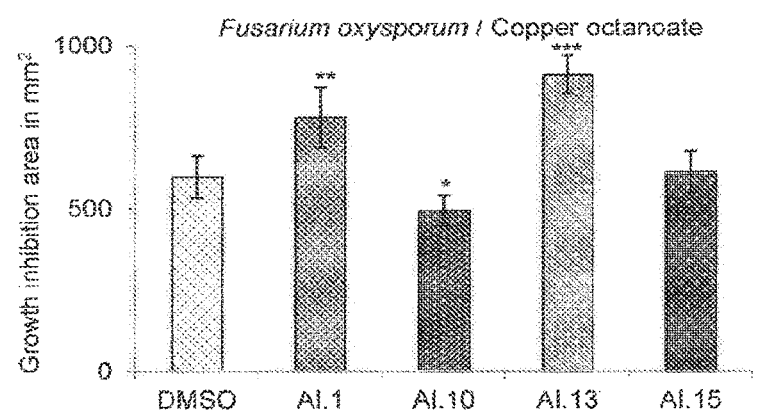
FIGS. 4A to 4C are graphs that show that Apyrase Inhibitors differentially enhance the potency of three different fungicides 4A. Copper Octanoate, 4B. Propiconazole, and 4C. Myclobutanil against the pathogenic fungi *Fusarium oxysporum*. Plant pathogenic fungi strain (*Fusarium oxysporum*) were grown in YPD medium petri dish in the presence of 65 µM of apyrase inhibitors (AI #1, 10, 13 and 15) at 30° C. for 12 days. The equivalent volume of dimethylsulphoxide (DMSO) was added as a control. The studies were repeated two times with similar results. Error bars indicate standard deviations (n=5). The significances of the potency of fungicides are indicated: * (Student's t-test, P<0.001); (Student's t-test, P<0.01) or *(Student's t-test, P<0.05).
Figure 4B:
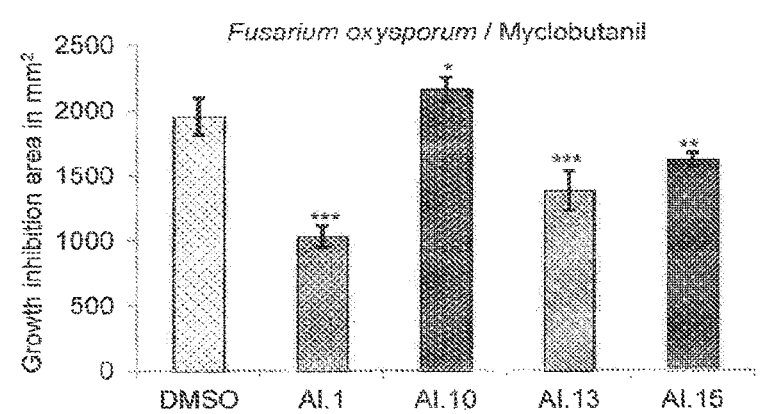
Figure 4C:
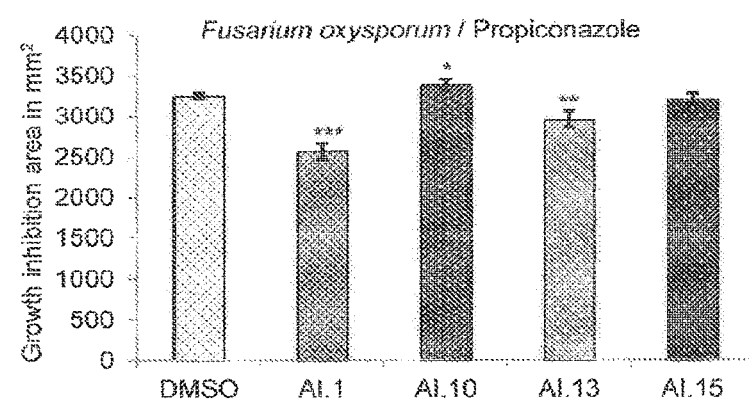
Figure 5A:
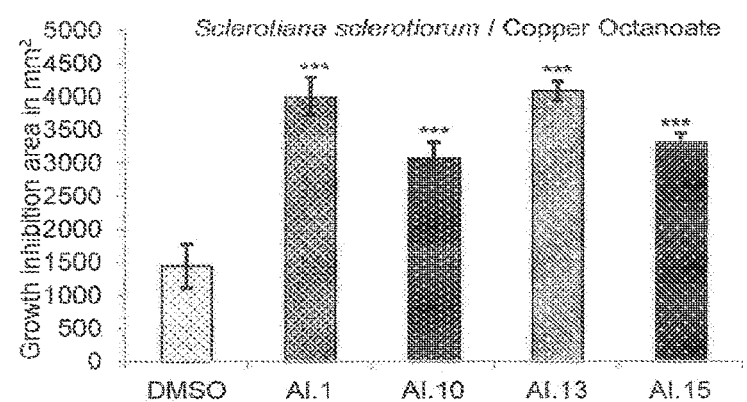
FIGS. 5A to 5C are graphs that show that Apyrase Inhibitors differentially enhance the potency of three different fungicides 5A. Copper Octanoate, 5B, Propiconazole, and 5C. Myclobutanil against the pathogenic fungi *Sclerotiana sclerotiorum*. Plant pathogenic fungi strain (*Sclerotiana sclerotiorum*) were grown in YPD medium petri dish in the presence of 65 µM of apyrase inhibitors (AI #1, 10, 13 and 15) at 30° C. for 7 days. The equivalent volume of dimethylsulphoxide (DMSO) was added as a control. The studies were repeated two times with similar results. Error bars indicate standard deviations (n=5). The significances of the potency of fungicides are indicated: * (Student's t-test, P<0.001); (Student's t-test, P<0.01) or *(Student's t-test, P<0.05).
Figure 5B:
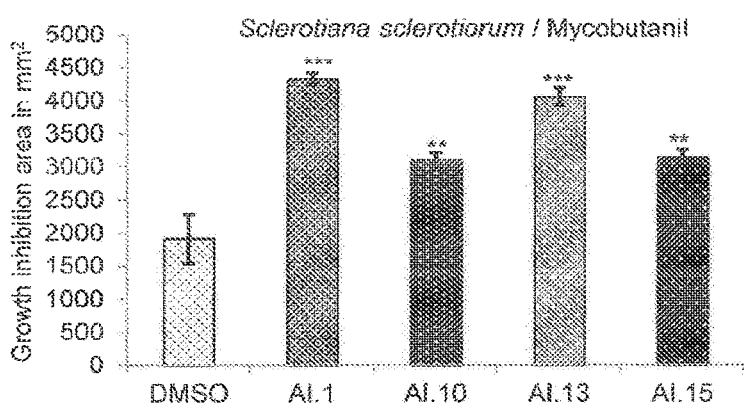
Figure 5C:
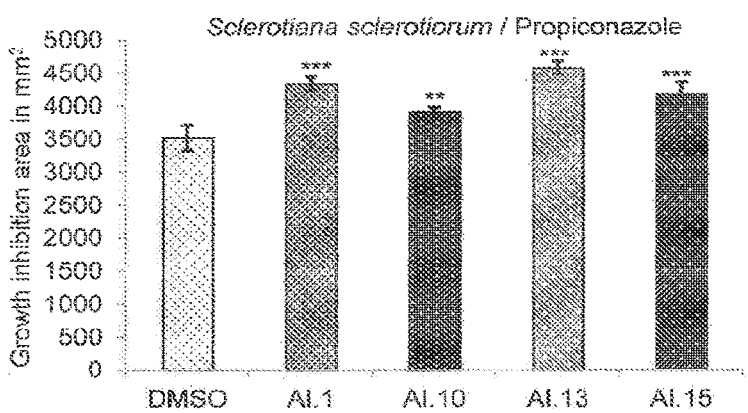

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

As used herein, the term "enhancer", "potentiator", refer to a compound or compounds that inhibit enzymatic apyrase activity (an "apyrase inhibitor", "AI" or "ai"), which leads to the enhancement, accentuation or potentiation of a fungicide. For example, when the enhancer or potentiator is used in conjunction with a fungicide, the combination of the potentiator and the fungicide enhances the fungicidal effect of the fungicide and/or renders a fungus that has become resistant to the fungicide susceptible to the fungicide as a result of the activity of the potentiator. Most often, these enhancers or potentiators have no untoward activity on the fungus itself or a living organism that is (or could be) infected with a fungus. The potentiators of the present invention are apyrase inhibitors that target fungal resistance to fungicides. Non-limiting examples of potentiators of the present invention include: N-(m-tolyl)-[1,1'-biphenyl]-4-sulfonamide (Apyrase Inhibitor I or (AI.1)); S-heptyl 2-oxo-2H-chromene-3-carbothioate; 3-(N-(4-bromophenyl) sulfamoyl)-N-(3-nitrophenyl)benzamide (AI.10); 3-(N-4-bromophenyl) sulfamoyl)-N-(3-nitrophenyl)benzamide (AI.13); and/or (E)-3-methyl-N-(1-(naphthalen-2-yl)ethylidene)benzohydrazide (AL.15). FIG. 7 shows exemplary chemical structures and systematic names of the studied apyrase inhibitors (AI). In certain embodiments, the fungicide enhancer or potentiator causes a sub-optimal amount of the fungicide to become optimal for treatment of the fungus, thereby reducing the amount of fungicide needed to treat the fungus. Given the increased resistance of fungi to fungicidal agents due to the overuse of fungicides, the present invention not only renders otherwise resistant fungi once again susceptible, it is also expected to reduce the opportunity for fungi to become resistant to fungicides as a result of using a lower dose regimen.

Apyrases are enzymes whose unifying characteristic is their ability to hydrolyze the gamma phosphate of ATP and, to a lesser extent, the beta phosphate of ADP. Most apyrases are expressed as plasma membrane associated proteins with their hydrolytic activity facing into the extracellular matrix. Extracellular apyrases are often referred to as euro-apyrases. Ecto-apyrases often hydrolyze extracellular ATP.

Fungal resistance to fungicides is often caused by the fungus developing the ability to quickly detoxify the fungicides by, e.g., sequestering the fungicide or exporting the fungicide across the plasma membrane. Fungi use diverse mechanisms for removing these xenobiotics, as such, countering this effect has been difficult. Inhibition of fungal resistance to xenobiotic detoxification would increase the potency of fungicides and/or render a fungi that has become resistant to fungicides susceptible again.

The compounds of this invention may be applied in the form of a composition comprising a fungicide, the apyrase inhibitor of the present invention with, e.g., an optional phytologically-acceptable carrier or diluent. These compositions will often be concentrated formulations that can be diluted in water, or another liquid, for application. In certain embodiments, the compositions can also be formulated into particles or granular formulations that are sprayed or applied without further treatment.

As used herein, the term "phytologically-acceptable" refers to compositions, diluents, excipients, and/or carriers that are generally applicable for use with any part of a plant during any part of its life cycle, including but not limited to seeds, seedlings, plant cells, plants, or flowers, The compositions can be prepared according to procedures, methods and formulas that are conventional in the agricultural arts. Following the teachings of the present invention the artist skilled in the agricultural and/or chemical arts can readily prepare a desired composition. Most commonly, the compounds of the present invention can be formulated to be stored, and/or applied, as aqueous or non-aqueous suspensions or emulsions prepared neat or from concentrated formulations of the compositions. Water-soluble, water-suspendable or emulsifiable formulations can also be converted into or formulated as solids (e.g., wettable powders), which can then be diluted into a final formulation. In certain formulations, the compositions of the present invention can also be provided in growth media, e.g., in vitro media for growth of plant or other types of cells, in laboratory plant growth media, in soil, or for spraying on seeds, seedlings, roots, stems, stalks, leaves, flowers or the entire plant.

The present inventors recognized that the ability of apyrase inhibitors to suppress the export of herbicides from plant cells by inhibiting ABCB transport activity raised the possibility that they could suppress the export of fungicides from pathogenic fungi and thus enhance the potency of fungicides. ABC transporters play a key role in aiding the resistance of pathogenic fungi to fungicides by exporting fungicides (Kretschmer et al., 2009). It was not possible to predict that plant apyrase inhibitors could be effective against fungal ABC transporters (as they are against plant ABCB transporters) or that they could enhance the fungicidal potency of fungicides, just as they enhance the herbicidal potency of herbicides.

Apyrases are well studied in animal cells and plant cells but are less well characterized in plant pathogenic fungi (Knowles et al., 2011; Clark et al., 2014). Fungal ectophosphatases are better characterized and can also hydrolyze ATP and ADP even though their $K_m$ for these, substrates is much higher than that of apyrases. Ectophosphatases have been shown to play important roles in processes of nutrition, proliferation, differentiation, adhesion, virulence and infection, so they could affect fungal resistance to fungicide in other ways. Adhesion to host cells is the first step in establishing a fungal infection and ectophosphatases may be one of the first parasite proteins that come into contact with the host cells. Several results indicate that ectophosphatase activities increase the potency of fungi to adhere to the host cells (Freitas-Mesquita A L et al., 2014).

The present invention demonstrates for the first time that specific apyrase inhibitors enhance the potency of the commonly available fungicides to more effectively restrict the growth of several plant pathogenic fungal species. In certain non-limiting embodiments, the apyrase inhibitors can be provided at: 0.01, 0.05, 0.1, 0.5, 1.0, 1.1, 1.2, 1.3, 1.4, 1.5, 1.6, 1.7, 1.8, 1.9, 2.0, 2.5, 3.0, 4.0, 5.0, 7.5, and 10% weight to weight in a final composition. When provided in liquid form, the apyrase inhibitors can be provided at: 0.01, 0.05, 0.1, 0.5, 1.0, 1.1, 1.2, 1.3, 1.4, 1.5, 1.6, 1.7, 1.8, 1.9, 2.0, 2.5, 3.0, 4.0, 5.0, 7.5, and 10% volume to volume in a final diluted composition. The skilled artisan will recognize that the formulation of the fungicide and the apyrase inhibitor can be provided in a concentrate that can be diluted prior to use, or can be provided in a diluted form ready for treatment.

For testing purposes, the various fungicides and inhibitors used with the present invention were used at certain concentrations. The skilled artisan will recognize that the various compositions as used commercially at varying concentrations and formulations. For example, it is common for fungicides to be applied commercially at 14-30% concentrations due to, e.g., environmental regulations. The present invention found particular uses with various fungicides known to have become less effective as a result of increased fungal resistance, e.g., copper and triazole fungicides.

For example, Propiconazole is a member of the triazole class of fungicides, the largest group of fungicides by market share. Propiconazole is used on fruits, vegetables, row crops and turf grasses to control a variety of fungal diseases. Myclobutanil is also a member of the triazole class of fungicides. Myclobutanil is used on fruits, vegetables, row crops and turf grasses to control a variety of fungal diseases.

Copper Octanoate is a member of the copper compounds class of fungicides, which is the second largest class of fungicides used in lite United States by market share. Copper Octanoate is used primarily on fruits and vegetables to control a variety of fungal diseases.

The present invention seeks to provide fungicide formulations particular effective against the plant fungal pathogens, for example, *Botrytis cinerea, Colletotrichum*

*graminicola, Fusarium oxysporum, Sclerotiana sclerotiorum, Verticillium dahlia, Mycospharella gramincola* and *Sphacelotheca reliana*.

*Botrytis cinerea* is an airborne plant pathogen with a necrotrophic lifestyle attacking over 200 crop hosts worldwide. It mainly attacks dicotyledonous plant species, including important protein, oil, fiber and horticultural crops, grapes and strawberries. Many classes of fungicides have failed to control *Botrytis cinerea* due to its genetic plasticity (Williamson et al., 2007). *Botrytis* also causes secondary soft rot of fruits and vegetables during storage, transit and at the market (González et al., 2006).

The genus *Colletotrichum* comprises ~600 species attacking over 3,200 species of monocot and dicot plants. *Colletotrichum graminicola* primarily infects maize (*Zea mays*), causing annual losses of approximately 1 billion dollars in the United States alone (Connell et al., 2012).

Fusarium wilt of banana, caused by the soil-borne fungus *Fusarium oxysporum* f.sp. *cubense*, was first reported in Australia in 1874. *Fusarium* wilt of banana is a major threat to banana production worldwide. No fungicides are currently available to effectively control the disease once plants are infected (Peng J et al., 2014).

The white mold fungus *Sclerotinia sclerotiorum* is known to attack more than 400 host species and is considered one of the most wide ranging plant pathogens. The majority of these species are dicotyledonous, along with a number of agriculturally significant monocotyledonous plants (Bolton et al., 2006). Some important crops affected by *S. sclerotiorum* include legumes (soybean), most vegetables, stone fruits and tobacco.

The ascomycete *Verticillium dahliae* is a soil-borne fungal plant pathogen that causes vascular wilt diseases in a broad range of dicotyledonous host species (Klosterman et al., 2009). *V. dahliae* can cause severe yield and quality losses in cotton and other important crops such as vegetables, fibers, fruit, nut trees, forest trees and ornamental plants (Bhat and Subbarao, 1999; Pegg and Brady, 2002).

The ascomycete fungus *Mycospharella gramincola* (anamorph: Septoria tritici) is one of the most important foliar diseases of wheat leaves, occurring wherever wheat is grown. Yield losses attributed to this disease range from 25%-50%, and are especially high in Europe, the Mediterranean region and East Africa. Infection by *M. gramincola* is initiated by air borne ascopores produced on residues of last season's crop. Primary infection usually occurs after seedlings emerge in spring or fall. The mature disease is characterized by necrotic lesions on the leaves and stems of infected plants.

The basidiomycete fungus *Sphacelotheca reliana* infects corn (*Zea mays*) systemically, causing Head Smut. Yield loss attributed to the disease is variable, and is directly dependent on the incidence of the disease. The fungus overwinters as diploid teliospores in crop debris or soil. Floral structures are converted to sort containing masses of powdery teliospores that resemble mature galls of common smut.

The plant pathogenic fungal strains *Botrytis cinerea, Colletotrichum graminicola, Fusarium oxysporum, Sclerotiana sclerotiorum* and *Verticillium dahliae* were obtained from the Institute for Plant Genomics & Biotechnology, Texas A & M University, USA Potato dextrose agar (PDA, Sigma-Aldrich) was routinely used for the growth of different pathogenic fungal strain.

Ectophosphatase inhibitors NGXT191 (AI.1), AI.10, NGXT1913 (AI.13), and AI. 15 were used dal this study. The fungicides copper octanoate ($C_{16}H_{30}CuO_4$), myclobutanil ($C_{15}H_{17}ClN_4$) and propiconazole ($C_{15}H_{17}Cl_2N_3O_2$) were used. The concentrations of these compounds used were copper octanoate (285 mM), myclobutanil (53.6 mM) and propiconazole (418 mM).

Fungal Growth Test:

Standard antifungal susceptibility disk tests were performed to determine any potentiating effect of ectophosphatase inhibitors on the growth of pathogenic fungus. The pathogenic fungus wild-type strains were plated on PDA medium with paper-disks containing, fungicides at the center of the plate. Plates containing either ectophosphatase inhibitors (65 μM) or an equal concentration of DMSO solvent (served as a control), which, when applied alone, did not affect the growth of pathogenic fungi. Plates were incubated at 30° C. for 7-days (*C. graminicola* and *S. sclerotiorum*) or 12-days (*B. cinerea, F. oxysporum* and *V. dahliae*), depending on the growth rate of the fungi. Plates were photographed, and the zone of fungal growth inhibition was measured by using IMAGE J™ software (NIH, USA). All the tests were performed with 5 replicates. The studies were performed two times. Results were analyzed for significance using Student T-tests.

Sequence and Phylogenetic Analysis of Apyrase:

Comparison of the deduced amino-acid sequence of apyrase (nucleoside triphosphate-diphosphohydrolases) from different plants and pathogenic fungi. *Arabidopsis thaliana* apyrase 1 (Accession No. NP_187058), *Arabidopsis thaliana* apyrase 2 (Accession No. NP_901154717), *Pisum sativum* (Accession No. BAA75506), *Botrytis cinerea* (Accession No. XP_001558134), *Collelotrichum graminicola* (Accession No. EFQ33146), *Fusarium oxysporum* (Accession No. ENH75262), *Sclerotiana sclerotiorum* (Accession No. XP_001590729) and *Verticillium dahliae* (Accession No. EGY20804) was made. A multiple alignment of the deduced amino acid sequences revealed that the primary structure of the apyrases from different pathogenic fungi differ in the size of their C-terminal ends from other known plant apyrases but retain functionally important conserved GDA1/CD39 (nucleoside phosphatase) superfamily domains. Out of the five fungi studied, *B. cinerea* has no nucleotide-binding region of the sugar kinase/HSP70/actin superfamily domain, but this region is present in *C. graminicola, F. oxysporum, S. sclerotiorum* and *V. dahliae*. The phylogenetic tree shows *C. graminicola* and *V. dahliae* are close to each other and lie on the same branch, whereas *B. cinerea, F. oxysporum* and *S. sclerotiorum* lie on different branches (FIG. 1).

Apyrase inhibitors inhibit the growth of plant fungal pathogen:

The following examples of ectophosphatase (apyrase) inhibitors were used in this study:

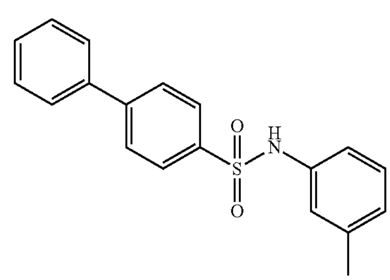

Formula: $C_{19}H_{17}NO_2S$

NAME: N-(m-tolyl)-[1,1'-biphenyl]-4-sulfonamide

AL1: N-(m-tolyl)-[1,1'-biphenyl]-4-sulfonamide.

-continued

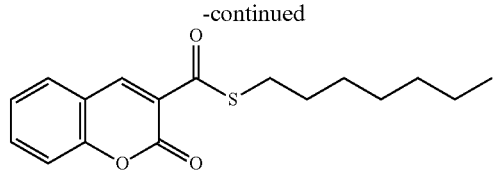

Formula: C₁₇H₂₀O₃S
NAME: S-heptyl 2-oxo-2H-chromene-3-carbothioate
AL10: S-heptyl 2-oxo-2H-chromene-3-carbothioate.

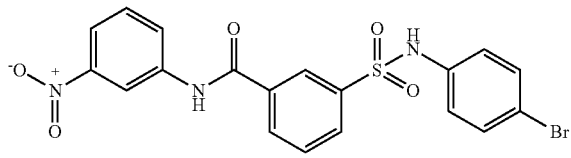

Formula: C₁₉H₁₄N₃O₅SBr
NAME: 3-(N-(4-bromophenyl)sulfamoyl)-N-
(3-nitrophenyl)benzamide
AL13: 3-(N-(4-bromophenyl)sulfamoyl)-N-
(3-nitrophenyl)benzamide.

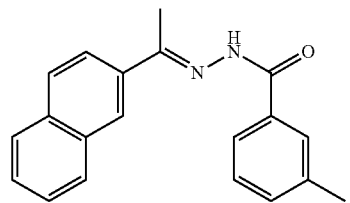

Formula: C₂₀H₁₈N₂O
NAME: (E)-3-methyl-N'-(1-(naphthalen-2-yl)
ethylidene)benzohydrazide
AL15: (E)-3-methyl-N'-(1-(naphthalen-2-yl)
ethylidene)benzohydrazide.

Figure 6A:
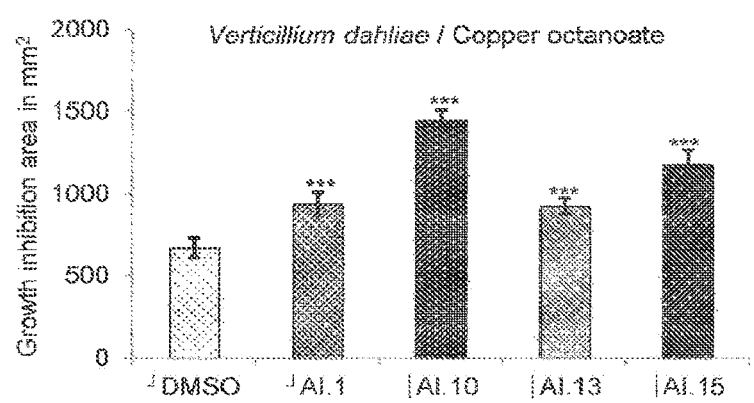
FIGS. 6A to 6C are graphs that show that Apyrase Inhibitors differentially enhance the potency of three different fungicides 6A. Copper Octanoate, 6B. Propiconazole, and 6C. Myclobutanil against the pathogenic fungi *Verticillium dahliae*. Plant pathogenic fungi strain (*Verticillium dahliae*) were grown in YPD medium petri dish in the presence of 65 µM of apyrase inhibitors (AI #1, 10, 13 and 15) at 30° C. for 12 days. The equivalent volume of dimethylsulphoxide (DMSO) was added as a control. The studies were repeated two times with similar results. Error bars indicate standard deviations (n=5). The significances of the potency of fungicides are indicated: * (Student's t-test, P<0.00)); (Student's t-test, P<0.01) or *(Student's t test, P<0.05).
Figure 6B:
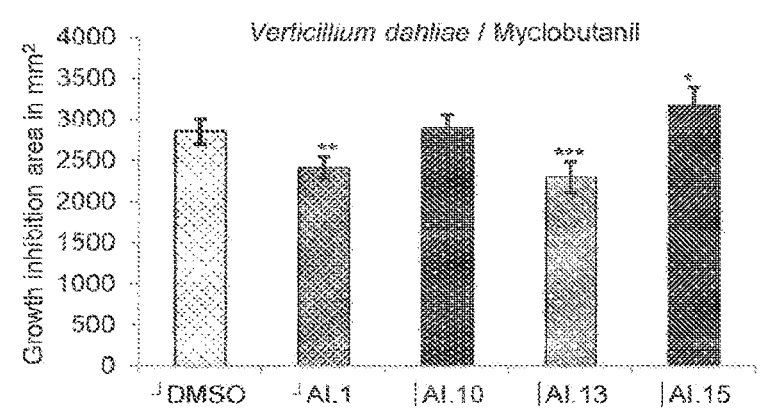
Figure 6C:
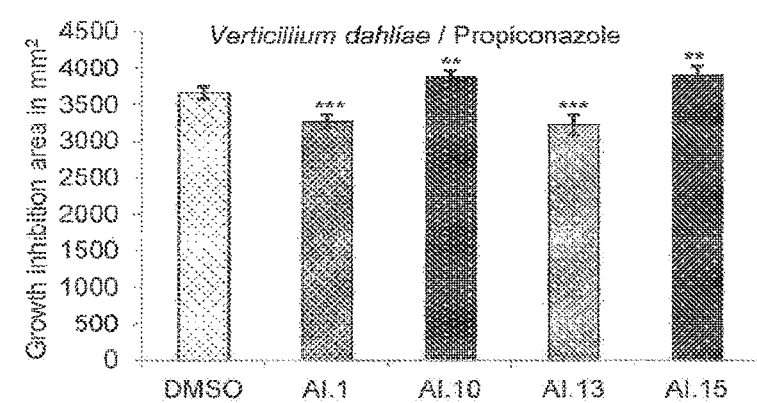

These apyrase inhibitors differentially enhanced the effect of copper compound and triazole fungicides (copper octanoate, myclobutanil, propiconazole, tebuconazole or epoxiconazole) against the plant pathogenic fungi, as judged by the plate assays used (Wang et al., 2012) and described in detail in the following sections.

When each of the compounds, abbreviated for convenience as: AI.1, AI.10, AI.13 and AI.15 (above), respectively, were tested alone in fungal plate assays, no fungicidal activity was detected. The tested apyrase inhibitors showed no effected on fungal growth.

EXAMPLE 1

*Botrytis Cinerea*

Pathogenic fungus *B. cinerea* was grown in the presence of fungicides (Copper octanoate, Myclobutanil and Propiconazole) supplemented with apyrase inhibitors AI.1, AI.10, AI.13 and AI. 15. Copper octanoate combined with inhibitor AI.1 had a significantly greater inhibitory effect on the growth of *B. cinerea* (22%) as compared to copper octanoate alone (FIG. 2A). Also myclobutanil combined with inhibitors AI.1, AI.13 and AI.15, had a significantly greater inhibitory effect on the growth of *B. cinerea* compared to that of myclobutanil alone (FIG. 2B). The fungicide propiconazole combined with inhibitors AI.1, AI.10 and AI.15 had a greater inhibitory effect on the growth of *B. cinerea* compared to propiconazole alone (FIG. 2C).

EXAMPLE 2

*Colletotrichum Graminicola*

Pathogenic fungus *C. graminicola* was grown in the presence of fungicides (copper octanoate, myclobutanil and propiconazole) supplemented with apyrase inhibitors AI.1, AI10, AI.13 and AI.15. Copper octanoate combined with inhibitors AI.1 and AI.13 had a significantly greater inhibitory effect on the growth of *C. graminicola* compared to that of copper octanoate alone (FIG. 3A). In the presence of inhibitors AI.1, AI.10, AI.13 and AI.15, fungicide myclobutanil had a significantly greater inhibitory effect on the growth of *C. graminicola* compared to that of myclobutanil alone (FIG. 3B). None of the four inhibitors along with propiconazole were able to inhibit the growth of fungus more significantly than the propiconazole used alone (FIG. 3C).

EXAMPLE 3

*Fusarium Oxysporum* f.sp Cubense

Pathogenic fungus *F. oxysporum* was grown in the presence of fungicides (copper octanoate, myclobutanil and propiconazole) supplemented with apyrase inhibitors AI.1, AI.10, AI.13 and AI.15. Copper octanoate combined with inhibitors AI.1 and AI.13 had a significantly greater inhibitory effect on the growth of *F. oxysporum* than copper octanoate alone (FIG. 4A). Fungicide myclobutanil in the presence of inhibitor AI.10 had a significantly greater inhibitory effect on the growth of *F. oxysporum* than myclobutanil alone (FIG. 4B). In the presence of AI.10 fungicide propiconazole had a significantly greater inhibitory effect on the growth of *F. oxysporum* than propiconazole alone (FIG. 4C).

EXAMPLE 4

*Sclerotiana sclerotiorum*

Pathogenic fungus *Sclerotiana sclerotiorum* was grown in the presence of fungicides (copper octanoate, myclobutanil and propiconazole) supplemented with apyrase inhibitors AI.1, AI.10, AI.13 and AI.15. Copper octanoate combined with inhibitors AI.1, AI.10, AI.13 and AI.15 had a significantly greater inhibitory effect on the growth of *Sclerotiana sclerotiorum* than copper octanoate alone (FIG. 5A). Myclobutanil in the presence of inhibitors AI.1, AI.10, AI13 and AI.15 had a significantly greater inhibitory effect on growth of *Sclerotiana sclerotiorum* than myclobutanil (FIG. 5B) alone. The fungicide propiconazole combined with inhibitors AI.1, AI.10, AI.13 and AI.15 had a significantly greater inhibitory effect on the growth of *Sclerotiana sclerotiorum* than propiconazole alone (FIG. 5C).

EXAMPLE 5

*Verticillium Dahliae*

Pathogenic fungus *V. dahliae* was grown in the presence of fungicides (copper octanoate, myclobutanil and propiconazole) supplemented with apyrase inhibitors AI.1, AI.10, AI.13 and AI.15. Copper octanoate combined with inhibitors AI.1, AI.10, AI.13 and AI.15 had a significantly greater inhibitory effect on the growth of fungus *V. dahliae* than copper octanoate alone (FIG. 6A). Myclobutanil combined with inhibitor AI.15 had a significantly greater inhibitory effect on the growth of *V. dahliae* than myclobutanil alone (FIG. 6B). Propiconazole in the presence of inhibitors AI.10 and AI.15 had a significantly greater inhibitory effect on the growth of *V. dahliae* than propiconazole alone (FIG. 6C).

EXAMPLE 6

Tebuconazole and AI

The compounds were tested for disease efficacy in combination with RAXIL® fungicide (tebuconazole), along with a low rate of metalaxyl on wheat seed. Rates of tebuconazole, 0.15 and 0.2.5 gm ai/100 kg, tested in combination with Enhancer AI.1 were 7.5 and 10 times below the commercial application rate of 1.5 gm ai/100 kg. The disease screens were pre-run with the reduced rates of tebuconazole and metalaxyl to assure lack of efficacy at these lower rates. Triazole at the standard rate of 1.5 gm ai/100 kg was included in the study as a control. The products were applied both as an over-treatment on seed pre-treated with the tebuconazole metalaxyl combination and as a single aqueous slurry with the two fungicides. Two rates, 2.5 and 10 gm ai/100 kg, of Enhancer AI.1 was evaluated.

Seedborne Bioassays. The seedborne bioassays are performed in sterile enclosed boxes that enable seedborne fungal pathogens to be detected. Plastic shoeboxes are surface sterilized and sterile blotter papers are placed in the bottom of each container. Monocot evaluations differ from dicot evaluations based on methods used to kill the seeds. Monocots are placed on blotters moistened with sterile water and allowed to incubate at 25° C. for 1 day followed by placement in 0° C. for 24 hours to kill the seed embryo. Dicot seeds are placed on blotters imbibed with a mild solution of 2,4-D herbicide used to kill the embryos. Bioassay boxes are then placed at 25° C. for 7 days. Fungal growth is observed and noted through microscope evaluation of each seed. Two replications of 50 seeds each are normally done. Results are provided in Table 1.

TABLE 1

Seedborne disease efficacy of RAXIL ® fungicide (tebuconazole) and Enhancer AI.1 seed treatments.

| Treatment | Total fungal counts * Var. A | Total fungal counts * Var. B |
|---|---|---|
| Untreated | 56 | 69 |
| Raxil @ 1.5 gm ai/100 kg | 20 | 25 |
| Raxil @ 0.25 gm ai/100 kg | 28 | 36 |
| Raxil @ 0.25 gm ai/100 kg + Enhancer 1 @ 2.5 gm ai/100 kg | 11 | 29 |
| Raxil @ .15 gm ai/100 kg | 23 | 46 |
| Raxil @ 0.15 gm ai/100 kg + Enhancer 1 @ 2.5 gm ai/100 kg | 9 | 21 |

* Fungal populations were combined counts for populations of *Alternaria*, *Aspergillus*, *Fusarium*, *Penicillium*, and *Cladosporium*

NSL+ Test. A natural sandy loam screen (NSL) is composed of a 1:1 mixture of sand to loam, in which the loam is naturally infested with *Pythium* spp. and other microbes endemic to the soil. The NSL+ test maintains the same soil mixture and an additional component of *Fusarium graminearum*. An appropriate isolate of *F. graminearum* was inoculated into the seed zone. Planted seeds are placed into a 10° C. atmosphere to allow for an optimum environment for Pythium pressure. Following 10 days under the above described conditions; seeds were moved to the greenhouse (27° C.) for seedling emergence and survival evaluation. The NSL+ test allows for evaluation of a compound for both *Pythium* and *Fusarium* activity in the same assay, similar to typical field conditions. All treatments were replicated five times and placement in the greenhouse was randomized. Emergence and survival of seedlings was evaluated. A sterile control was included in all screenings. The sterile control was composed of untreated seeds being placed in a sterilized NSL mixture. Results are provided in Tables 2 and 3.

TABLE 2

| Treatment | Stand % After 21 Days |
|---|---|
| Untreated | 20 |
| Raxil @ 1.5 gm ai/100 kg | 96 |
| Raxil @ .25 gm ai/100 kg | 84 |
| Raxil @ .25 gm ai/100 kg + A.I. #1 @ 2.5 gm ai/100 kg | 96 |
| Raxil @ .15 gm ai/100 kg | 80 |
| Raxil @ .15 gm ai/100 kg + A.I. #1 @ 2.5 gm ai/100 kg | 88 |
| Sterile Control | 100 |

TABLE 3

Field trial shows enhancement of Raxil (tebuconazole) against Head Smut (Sphacelotheca reiliana) in Corn.

| Treatment | Treatment Type | Stand Count | Overall % Infected Plants |
|---|---|---|---|
| Untreated Check | No Fungicide Control | 275 | 31.2 |
| Metalaxyl + Triadiminol @ 62 gms ai/100 kg | Label Rate of Control Fungicide | 293 | 24.2 |
| Metalaxyl + Triadiminol @ 20.7 gms ai/100 kg + A.I. #1 @ 10 gms ai/100 kg | ⅓ Rate of Control Fungicide + Enhancer #1 | 255 | 36.6 |
| Metalaxyl + Tebuconazole @ 7.5 gms ai/100 kg | Label Rate of Tebuconazole | 252 | 24.9 |
| Metalaxyl + Tebuconazole @ 2.5 gms ai/100 kg + A.I. #1 @ 10 gms ai/100 kg | ⅓ Label Rate of Tebuconazole + Enhancer #1 | 271 | 16 |

EXAMPLE 7

Comparison of Different Apyrase Inhibitors on Epoxiconazole Activity

Isolates were grown on Yeast Potato Dextrose agar. Fungicide sensitivity testing based on OD measurements was carried out in 96 well plates using approximately 10,000 spores per well (microscopy spore counts). Test concentrations of enhancers were 0, 0.003, 0.016, 0.08, 0.4, 2, 10 and 50 $\mu g\ ml^{-1}$. Fungicide concentrations tested were 0, 0.00128, 0.0064, 0.016, 0.032, 0.08, 0.16, 0.8, 4, 10, 20 and 50 $\mu ml^{-1}$. Results are provided in Tables 4 and 5.

TABLE 4

Effect of different apyrase inhibitors on the epoxiconazole susceptibility of *Mycosphaerella graminicola* isolate FLU4-02.

| Enhancer | Epoxiconazole $EC_{50}$ ($\mu g \, ml^{-1}$) | | | | | |
|---|---|---|---|---|---|---|
| Concentration ($\mu g \, ml^{-1}$) | Enhancer A.I.1 | Enhancer A.I. 2 | Enhancer A.I. 10 | Enhancer A.I. 12 | Enhancer A.I. 14 | Enhancer A.I. 16 |
| 0 | 0.091 | 0.078 | 0.084 | 0.088 | 0.077 | 0.073 |
| 0.003 | 0.071 | 0.075 | 0.074 | 0.074 | 0.08 | 0.072 |
| 0.016 | 0.073 | 0.058 | 0.066 | 0.066 | 0.07 | 0.07 |
| 0.08 | 0.044 | 0.064 | 0.065 | 0.065 | 0.077 | 0.068 |
| 0.4 | 0.018 | 0.080 | 0.078 | 0.078 | 0.086 | 0.069 |
| 2.0 | 0.002 | 0.076 | 0.073 | 0.075 | 0.086 | 0.069 |
| 10 | 0.002 | 0.077 | 0.083 | No growth | 0.098 | 0.081 |

Enhancer A.I.1 is N-(m-tolyl)-[1, 1'-biphenyl]-4-sulfonamide.
Enhancer A.I. 2 is 3-hexyl-2,3-dihydro-N,4-diphenylthiazol-2-ammoniumbromide.
Enhancer A.I. 10 is S-heptyl 2-oxo-2H-chromene-3-carbothioate.
Enhancer A.I. 12 is ethyl 2-[(N-cyclohexylglycyl) amino]-4,5,6,7-tetrahydro-1-benzothiophene-3-carboxylate.
Enhancer A.I. 14 is (E)-N'-(2-hydroxy-5-nitobenzylidene)hexanehydrazide.
Enhancer A.I. 16 is prop-2-ynyl 2-(4-chlorophenylcarbamoyl) benzoate.

TABLE 5

Effect of Enhancer A.I.1 on different fungicide susceptibility of *Septoria tritici* isolate G3-03.

| Enhancer A.I.1 Concentration | $EC_{50}$ ($\mu g \, ml^{-1}$) | | | | |
|---|---|---|---|---|---|
| ($\mu g \, ml^{-1}$) | Azoxystrobin | Carbendazim | Chlorothalonil | Cyprodinil | Epoxiconazole |
| 0 | 7.210 | >50 | 0.370 | 3.055 | 0.142 |
| 0.003 | 7.339 | >50 | 0.369 | 3.135 | 0.142 |
| 0.016 | 7.071 | >50 | 0.357 | 2.995 | 0.141 |
| 0.08 | 6.914 | >50 | 0.369 | 2.838 | 0.145 |
| 0.4 | 6.958 | >50 | 0.335 | 3.244 | 0.06 |
| 2.0 | 5.157 | >50 | 0.36 | 4.046 | 0.008 |
| 10 | 2.816 | >50 | 0.364 | 4.220 | 0.004 |

The compositions of this invention are applied to plants in the form of dispersions, solutions, suspensions, aerosols and powder, which comprise the fungicide and enhancer of this invention and a phytologically-acceptable inert carrier. The most widely used carrier is water. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention.

The actual amount of the composition to be applied the plants is not critical and can readily be determined by those skilled in the art. In general, concentrations from 10 ppm to 5000 ppm by weight of active compound are expected to provide good control. With many of the compounds, concentrations from 100 to 1500 ppm will suffice.

Plant fungal diseases can be controlled by applying effective amounts of the inventive composition to the plant pathogens or a place where the plant pathogens inhabit or a place (plant, soil) where the plant pathogens may inhabit. Plant diseases can be controlled by applying effective amounts of the compositions to a plant or a place where a plant is allowed to grow. Specifically application is made to the stalk and leaves of the plant, seed of the plant, bulbs of the plant including bulb, corm, rhizoma, stem tuber, root tuber and rhizophore.

As the treatment of the soil in the control method of the present invention, for example, spraying onto the soil, admixing with the soil, perfusion of an agent liquid into the soil (irrigation of an agent liquid, injection into the soil, dripping of an agent liquid) can be included. The treatment can be performed before dissemination, at the time of dissemination, immediately after the dissemination, during the raising period of seedlings, before settled planting, at the time of settled planting and growing time after settled planting.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed:

1. A composition comprising a fungicide comprising:
   a) copper octanoate, and an enhancer selected from N-(m-tolyl)-[1,1'-biphenyl]-4-sulfonamide, S-heptyl 2-oxo-2H-chromene-3-carbothioate, 3-(N-(4-bromophenyl) sulfamoyl)-N-(3-nitrophenyl)benzamide, or (E)-3-methyl-N'-(1-(naphthalen-2-yl)ethylidene);
   b) myclobutanil and an enhancer selected from N-(m-tolyl)-[1,1'-biphenyl]-4-sulfonamide, S-heptyl 2-oxo-2H-chromene-3-carbothioate, 3-(N-(4-bromophenyl) sulfamoyl)-N-(3-nitrophenyl)benzamide, or (E)-3-methyl-N'-(1-(naphthalen-2-yl)ethylidene) benzohydrazide;
   c) propiconazole and an enhancer selected from N-(m-tolyl)-[1,1'-biphenyl]-4-sulfonamide or 3-(N-(4-bromophenyl) sulfamoyl)-N-(3-nitrophenyl)benzamide;
   d) tebuconazole and an enhancer selected from N-(m-tolyl)-[1,1'-biphenyl]-4-sulfonamide, S-heptyl 2-oxo-2H-chromene-3-carbothioate or 3-(N-(4-bromophenyl) sulfamoyl)-N-(3-nitrophenyl)benzamide
   e) copper hydroxide and (E)-3-methyl-N'-(1-(naphthalen-2-yl)ethylidene) benzohydrazide;
   f) prothioconazole and (E)-3-methyl-N'-(1-(naphthalen-2-yl)ethylidene) benzohydrazide; or
   g) difenoconazole and (E)-3-methyl-N'-(1-(naphthalen-2-yl)ethylidene) benzohydrazide.

2. The composition of claim 1, wherein the composition further comprises a phytologically-acceptable inert carrier.

3. The composition of claim 1, wherein the amount of the fungicide is not effective for treating a fungus.

4. The composition of claim 1, wherein the amount of the fungicide is effective for treating a fungus and is adapted for application to a fungicide-resistant fungus.

5. The composition of claim 1, wherein the enhancer is provided at 0.005, 0.01, 0.05, 0.1, 0.5, 1.0, 1.1, 1.2, 1.3, 1.4, 1.5, 1.6, 1.7, 1.8, 1.9, 2.0, 2.5, 3.0, 4.0, 5.0, 7.5, or 10% weight to weight enhancer to fungicide.

6. The composition of claim 1, wherein the enhancer is provided at 0.005, 0.01, 0.05, 0.1, 0.5, 1.0, 1.1, 1.2, 1.3, 1.4, 1.5, 1.6, 1.7, 1.8, 1.9, 2.0, 2.5, 3.0, 4.0, 5.0, 7.5, or 10% volume to volume enhancer to fungicide.

7. The composition of claim 1, wherein the composition is synergistic and the weight ratio of the fungicide to the enhancer is between about 500:1 and 5000:1.

8. A fungicide comprising:
   a) copper octanoate; and an apyrase inhibitor selected from N-(m-tolyl)-[1,1'-biphenyl]-4-sulfonamide, S-heptyl 2-oxo-2H-chromene-3-carbothioate, 3-(N-(4-bromophenyl) sulfamoyl)-N-(3-nitrophenyl)benzamide, or (E)-3-methyl-N'-(1-(naphthalen-2-yl)ethylidene);
   b) myclobutanil and an enhancer selected from N-(m-tolyl)-[1,1'-biphenyl]-4-sulfonamide, S-heptyl 2-oxo-2H-chromene-3-carbothioate, 3-(N-(4-bromophenyl) sulfamoyl)-N-(3-nitrophenyl)benzamide, or (E)-3-methyl-N'-(1-(naphthalen-2-yl)ethylidene) benzohydrazide;
   c) propiconazole and an enhancer selected from N-(m-tolyl)-[1,1'-biphenyl]-4-sulfonamide or 3-(N-(4-bromophenyl) sulfamoyl)-N-(3-nitrophenyl)benzamide;
   d) tebuconazole and an enhancer selected from N-(m-tolyl)-[1,1'-biphenyl]-4-sulfonamide, S-heptyl 2-oxo-2H-chromene-3-carbothioate or 3-(N-(4-bromophenyl) sulfamoyl)-N-(3-nitrophenyl)benzamide
   e) copper hydroxide and (E)-3-methyl-N'-(1-(naphthalen-2-yl)ethylidene) benzohydrazide;
   f) prothioconazole and (E)-3-methyl-N'-(1-(naphthalen-2-yl)ethylidene) benzohydrazide; or
   g) difenoconazole and (E)-3-methyl-N'-(1-(naphthalen-2-yl)ethylidene) benzohydrazide, in amounts sufficient to treat a fungus.

9. The fungicide of claim 8, wherein the fungicide is added to a growth media for growing cells.

10. The fungicide of claim 8, wherein the cells are selected from at least one of bacterial, fungal, plant, animal, mammalian, yeast, amphibian, avian, nematode or insect cells.

11. The fungicide of claim 8, wherein the composition is synergistic and the weight ratio of the fungicide to the apyrase inhibitor is between about 500:1 and 5000:1.

\* \* \* \* \*